United States Patent [19]
Kirsch et al.

[11] Patent Number: 5,961,880
[45] Date of Patent: Oct. 5, 1999

[54] 1,3-DIOXANE DERIVATIVES HAVING AXIAL FLUORINE SUBSTITUTION

[75] Inventors: Peer Kirsch, Darmstadt; Kazuaki Tarumi, Seeheim; Joachim Krause, Dieburg, all of Germany

[73] Assignee: Merck Patent Gesellschaft mit Beschrankter Haftung, Germany

[21] Appl. No.: 09/090,341

[22] Filed: Jun. 4, 1998

[30] Foreign Application Priority Data

Jun. 4, 1997 [DE] Germany ............... 197 23 277

[51] Int. Cl.⁶ ............... C09K 19/34; C07D 319/06; G02F 1/13
[52] U.S. Cl. ............... 252/299.61; 549/369; 349/182
[58] Field of Search ............... 252/299.61; 549/369; 349/182

[56] References Cited

U.S. PATENT DOCUMENTS 4,510,069 4/1985 Eidenschink et al. ............... 252/299.61

FOREIGN PATENT DOCUMENTS 0 381 531 8/1990 European Pat. Off. .
2 248 059 9/1991 United Kingdom .

OTHER PUBLICATIONS

T. Ishihara et al., *J. Org. Chem.*, vol. 55, pp. 3107–3114 (1990).
J. Dubois et al., *Tetrahedron*, vol. 47, No. 6, pp. 1001–1012 (1991).
T. Yamazaki et al., *J. Org. Chem.*, vol. 54, pp. 83–91 (1989).

*Primary Examiner*—C. H. Kelly
*Attorney, Agent, or Firm*—Millen, White, Zelano, & Branigan, P.C.

[57] ABSTRACT

1,3-Dioxane compounds of the formula I $$R^1-(A^1-Z^1)_m-W-(Z^2-A^2)_n-R^2 \quad (I)$$

in which
W is

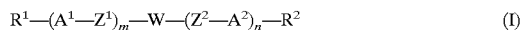

and
$R^1$, $R^2$, $A^1$, $A^2$, $Z^1$, $Z^2$, m, n,

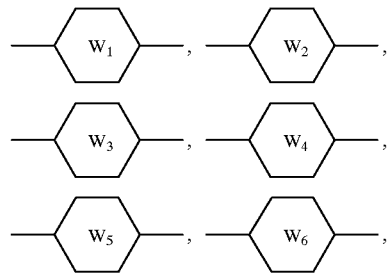

$n_1$, $n^2$, $n_3$, $n_4$, $n_5$, $n_6$, $Z^3$ and $Z^4$ are as defined herein, are suitable as components of liquid-crystalline media.

12 Claims, No Drawings

1,3-DIOXANE DERIVATIVES HAVING AXIAL FLUORINE SUBSTITUTION

The invention relates to 1,3-dioxane derivatives having axial fluorine substitution, of the general formula I

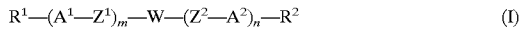   (I)

in which
W is

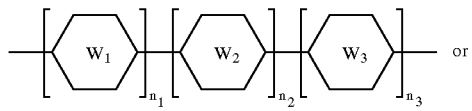   or

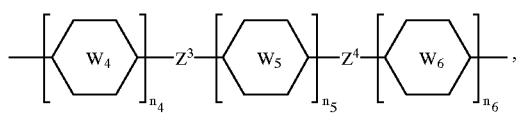, where

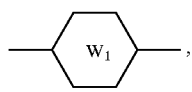,

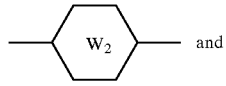 and

are each, independently of one another,

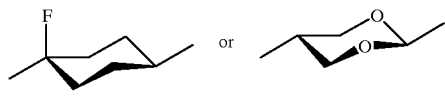

$n_1$, $n_2$ and $n_3$ are each, independently of one another, 0 or 1,
where one of the groups

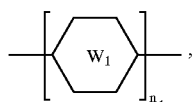,

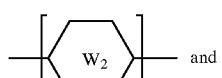 and

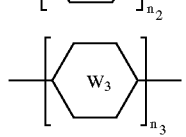

must be

, and another of these groups must simultaneously be

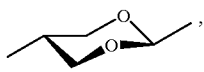,

,

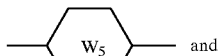 and

are each, independently of one another,

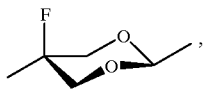,

 or

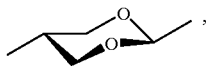, $n_4$, $n_5$ and $n_6$ are each, independently of one another, 0 or 1,
where one of the groups

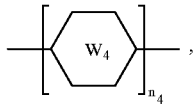,

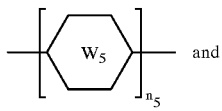 and

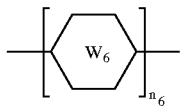

must be

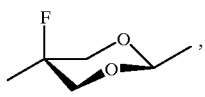, $R^1$ and $R^2$ are each, independently of one another,
an alkyl or alkenyl radical having 1 to 12 carbon atoms which is unsubstituted, mono-substituted by CN or $CF_3$ or at least mono-substituted by halogen, (e.g., up to perhalosubstituted) where one or more $CH_2$ groups in these radicals may also be replaced, independently of one another, by —O—, —S—, —CO—, —CO—O—, —O—CO— or —O—CO—

O— in such a way that hetero atoms are not linked directly to one another, $R^2$ is alternatively F, Cl or CN, $A^1$ and $A^2$ are each, independently of one another,
 a) a trans-1,4-cyclohexylene radical in which, in addition, one or more non-adjacent $CH_2$ groups may be replaced by —O— and/or —S—,
 b) a 1,4-cyclohexenylene radical,
 c) a 1,4-phenylene radical, in which, in addition, one or two CH groups may be replaced by N, or
 d) a radical selected front the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, where the radicals a), b) and c) may be substituted by CN or F, $Z^1$, $Z^2$, $Z^3$ and $Z^4$ are each, independently of one another, —CO—O—, —O—CO—, —$CH_2$O—, —O$CH_2$—, —$CH_2CH_2$—, —CH=CH—, —C≡C— or a single bond, and m and n are each, independently of one another,
 0, 1, 2 or 3,
 where $n_1+n_2+n_3+m+n=2$, 3 or 4, and $n_4+n_5+n_6+m+n=1$, 2, 3 or 4.

The invention furthermore relates to the use of the compounds of the general formula I as components of liquid-crystalline media and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases (DAP) or ECB (electrically controlled birefringence) or the effect of dynamic scattering. The substances employed hitherto for this purpose all have certain disadvantages, for example inadequate stability to the action of heat, light or electric fields, or unfavorable elastic and/or dielectric properties.

Compounds which contain a 1- or 4-fluorocyclohexane-1,4-diyl unit are disclosed, for example, in GB 2,248,059 A and EP 0,107,759 B1, but no compounds which additionally contain a 1,3-dioxane-2,5-diyl unit are described therein.

Compounds which contain a 5-fluoro-1,3-dioxane-2,5-diyl unit are disclosed, for example, in J. Dubois, C. Foures, S. Bory, S. Falcon, M. Gaudry, A. Marquet, Tetrahedron (1991), 47 (6), 1001–1012;

EP 381 531 A2;

T. Ishihara, M. Kuroboshi, K. Yamaguchi, Y. Okada, J. Org. Chem. (1990), 55 (10), 3107–3114;

T. Yamazaki, T. Yamamoto, T. Kitazume, J. Org. Chem. (1989), 54 (1), 83–91, but the compounds described therein contain two methyl groups in position 2 of the 5-fluoro-1,3-dioxane-2,5-diyl unit.

The invention has an object of finding novel, stable, liquid-crystalline or mesogenic compounds which are suitable as components of liquid-crystalline media, in particular for TFT and STN displays.

Upon further study of the specification and appended claims, further objects and advantages of this invention will become apparent to those skilled in the art.

It has now been found that compounds of the formula I are eminently suitable as components of liquid-crystalline media. They can be used to obtain stable liquid-crystalline media, particularly suitable for TFT or STN displays. The novel compounds are distinguished by high thermal stability and have advantageous values for the holding ratio. The compounds of the formula I have, in particular, highly negative dielectric anisotropy Δε and are therefore particularly suitable for displays based on the effect of deformation of aligned phases. The compounds of the formula I according to the invention are furthermore distinguished by very low optical anisotropy values Δn and favorable phase behavior and good viscoelastic properties.

In addition, the provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

The meaning of the formula I includes all isotopes of the chemical elements bound in the compounds of the formula I.

In the pure state, the compounds of the formula I are colorless and form liquid-crystalline mesophases in a temperature range which is favorably located for electro-optical use. They are stable chemically, thermally and to light.

The invention thus relates to compounds of the formula I and to the use of these compounds as components of liquid-crystalline media. The invention furthermore relates to liquid-crystalline media containing at least one compound of the formula I, and to liquid-crystal display elements, in particular electro-optical display elements, which contain media of this type.

Above and below, $R^1$, $R^2$, $Z^1$, $Z^2$, $A^1$, $A^2$, W, m, n,

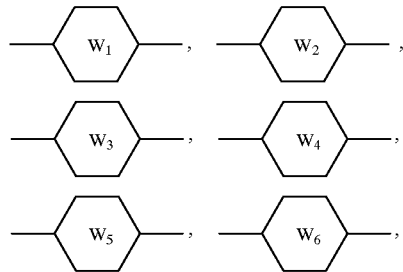

$n_1$, $n_2$, $n_3$, $n_4$, $n_5$, $n_6$, $Z^3$ and $Z^4$ are as defined above, unless expressly stated otherwise.

For reasons of simplicity, $Cyc^a$ below denotes a 1,4-cyclohexylene radical, Che denotes a 1,4-cyclo-hexenylene radical, Dio denotes a 1,3-dioxane-2,5-diylradical, Dit denotes a dithiane-2,5-diyl radical, $Phe^a$ denotes a 1,4-phenylene radical, Pyd denotes a pyridine-2,5-diyl radical, $Pyr^a$ denotes a pyridine-2,5-diyl radical and Bco denotes a bicyclo[2.2.2]-octylene radical, where $Cyc^a$ and/or $Phe^a$ may be unsubstituted or monosubstituted or polysubstituted by F or CN.

The compounds of the formula I according to the invention include, for example, compounds containing no ring in the mesogenic groups $R^1$—$(A^1$—$Z^1)_m$— and —$(Z^2$—$A^2)_n$—$R^2$, of the subformula II:

$$R^1\text{—W—}R^2 \qquad \text{I1,}$$

compounds containing one ring in the mesogenic groups $R^1$—$(A^1$—$Z^1)_m$— and —$(Z^2$—$A^2)_n$—$R^2$, of the subformulae I2 to I5:

$R^1-A^1-W-R^2$   I2

$R^1-A^1-Z^1-W-R^2$   I3

$R^1-W-A^2-R^2$   I4

$R^1-W-Z^2-A^2-R^2$   I5 compounds containing two rings in the mesogenic groups $R^1-(A^1-Z^1)_m-$ and $-(Z^2-A^2)_n-R^2$, of the subformula I6 to I17:

$R^1-A^1-A^1-W-R^2$   I6

$R^1-A^1-Z^1-A^1-W-R^2$   I7

$R^1-A^1-A^1-Z^1-W-R^2$   I8

$R^1-A^1Z^1-A^1-Z^1-W-R^2$   I9

$R^1-A^1-W-A^2-R^2$   I10

$R^1-A^1-Z^1-W-A^2-R^2$   I11

$R^1-A^1-W-Z^2-A^2-R^2$   I12

$R^1-A^1-Z^1-W-Z^2-A^2-R^2$   I13

$R^1-W-A^2-A^2-R^2$   I14

$R^1-W-Z^2-A^2-A^2-R^2$   I15

$R^1-W-A^2-Z^2-A^2-R^2$   I16

$R^1-W-Z^2-A^2-Z^2-A^2-R^2$   I17 and compounds containing three rings in the mesogenic groups $R^1-(A^1-Z^1)_m-$ and $-(Z^2-A^2)_n-R^2$, of the subformulae I18 to I49:

$R^1-A^1-A^1-A^1-W-R^2$   I18

$R^1-A^1-Z^1-A^1-A^1-W-R^2$   I19

$R^1-A^1-A^1-Z^1-A^1-W-R^2$   I20

$R^1-A^1-A^1-A^1-Z^1-W-R^2$   I21

$R^1-A^1-Z^1-A^1-Z^1-A^1-W-R^2$   I22

$R^1-A^1-Z^1-A^1-A^1-Z^1-W-R^2$   I23

$R^1-A^1-A^1-Z^1-A^1-Z^1-W-R^2$   I24

$R^1-A^1-Z^1-A^1-Z^1-A^1-Z^1-W-R^2$   I25

$R^1-A^1-A^1-W-A^2-R^2$   I26

$R^1-A^1-Z^1-A^1-W-A^2-R^2$   I27

$R^1-A^1-A^1-Z^1-W-A^2-R^2$   I28

$R^1-A^1-A^1-W-Z^2-A^2-R^2$   I29

$R^1-A^1-Z^1-A^1-Z^1-W-A^2-R^2$   I30

$R^1-A^1-Z^1-A^1-W-Z^2-A^2-R^2$   I31

$R^1-A^1-A^1-Z^1-W-Z^2-A^2-R^2$   I32

$R^1-A^1-Z^1-A^1-Z^1-W-Z^2-A^2-R^2$   I33

$R^1-A^1-W-A^2-A^2-R^2$   I34

$R^1-A^1-Z^1-W-A^2-A^2-R^2$   I35

$R^1-A^1-W-Z^2-A^2-A^2-R^2$   I36

$R^1-A^1-W-A^2-Z^2-A^2-R^2$   I37

$R^1-A^1-Z^1-W-Z^2-A^2-A^2-R^2$   I38

$R^1-A^1-Z^1-W-A^2-Z^2-A^2-R^2$   I39

$R^1-A^1-W-Z^2-A^2-Z^2-A^2-R^2$   I40

$R^1-A^1-Z^1-W-Z^2-A^2-Z^2-A^2-R^2$   I41

$R^1-W-A^2-A^2-A^2-R^2$   I42

$R^1-W-Z^2-A^2-A^2-A^2-R^2$   I43

$R^1-W-A^2-Z^2-A^2-A^2-R^2$   I44

$R^1-W-A^2-A^2-Z^2-A^2-R^2$   I45

$R^1-W-Z^2-A^2-Z^2-A^2-A^2-R^2$   I46

$R^1-W-Z^2-A^2-A^2-Z^2-A^2-R^2$   I47

$R^1-W-A^2-Z^2-A^2-Z^2-A^2-R^2$   I48

$R^1-W-Z^2-A^2-Z^2-A^2-Z^2-A^2-R^2$   I49.

Of these, particular preference is given to the subformulae I1, I2, I3, I4, I5, I6, I7, I10, I14 and I16.

The preferred compounds of the subformula I2 include those of the subformulae I2a and I2b:

$R^1-Phe^a-W-R^2$   I2a $R^1-Cyc^a-W-R^2$   I2b.

The preferred compounds of the subformula I3 include those of the subformulae I3a to I3c:

$R^1-Phe^a-Z^1-W-R^2$   I3a $R^1-Cyc^a-Z^1-W-R^2$   I3b $R^1-A^1-CH_2CH_2-W-R^2$   I3c.

The preferred compounds of the subformula I4 include those of the subformulae I4a and I4b:

$R^1-W-Phe^a-R^2$   I4a $R^1-W-Cyc^a-R^2$   I4b.

The preferred compounds of the subformula I5 include those of the subformulae I5a to I5c:

$R^1-W-Z^2-Phe^a-R^2$   I5a $R^1-W-Z^2-Cyc^a-R^2$   I5b $R^1-W-CH_2CH_2-A^2-R^2$   I5c.

The preferred compounds of the subformulae I6 include those of the subformulae I6a to I6g:

$R^1-Cyc^a-Cyc^a-W-R^2$   I6a $R^1-Cyc^a-Phe^a-W-R^2$   I6b $R^1-Phe^a-Phe^a-W-R^2$   I6c $R^1-Pyd-Phe^a-W-R^2$   I6d $R^1-Phe^a-Cyc^a-W-R^2$   I6e $R^1-Dio-Phe^a-W-R^2$   I6f $R^1-Pyr^a-Phe^a-W-R^2$   I6g.

Of these, particular preference is given to those of the subformulae I6a, I6b, I6c and I6e.

The preferred compounds of the subformula I7 include those of the subformulae I7a to I7h:

$R^1$—$Cyc^a$—$Z^1$—$Cyc^a$—W—$R^2$    I7a $R^1$—$A^1$—$CH_2CH_2$—$A^1$—W—$R^2$    I7b $R^1$—$Cyc^a$—$Z^1$—$Phe^a$—W—$R^2$    I7c $R^1$—$A^1$—OCO—$Phe^a$—W—$R^2$    I7d $R^1$—$Phe^a$—$Z^1$—$Phe^a$—W—$R^2$    I7e $R^1$—$Pyr^a$—$Z^1$—$A^1$—W—$R^2$    I7f $R^1$—Pyd—$Z^1$—$A^1$—W—$R^2$    I7g $R^1$—Dio—$Z^1$—$A^1$—W—$R^2$    I7h.

Of these, particular preference is given to those of the subformulae I7a, I7b, I7c and I7e.

The preferred compounds of the subformula I10 include those of the subformulae I10a to I10g:

$R^1$—$Cyc^a$—W—$Cyc^a$—$R^2$    I10a $R^1$—$Cyc^a$—W—$Phe^a$—$R^2$    I10b $R^1$—$Phe^a$—W—$Phe^a$—$R^2$    I10c $R^1$—Dio—W—$A^2$—$R^2$    I10d $R^1$—$A^1$—W—Dio—$R^2$    I10e $R^1$—$Phe^a$—W—$Cyc^a$—$R^2$    I10f $R^1$—$A^1$—W—Che—$R^2$    I10g.

Of these, particular preference is given to those of the subformulae I10a, I10b, I10c and I10f.

The preferred compounds of the subformula I14 include those of the subformulae I14a to I14g:

$R^1$—W—$Cyc^a$—$Cyc^a$—$R^2$    I14a $R^1$—W—$Phe^a$—$Cyc^a$—$R^2$    I14b $R^1$—W—$Phe^a$—$Phe^a$—$R^2$    I14c $R^1$—W—$Phe^a$—Pyd—$R^2$    I14d $R^1$—W—$Cyc^a$—$Phe^a$—$R^2$    I14e $R^1$—W—$Phe^a$—Dio—$R^2$    I14f $R^1$—W—$Phe^a$—$Pyr^a$—$R^2$    I14g.

Of these, particular preference is given to those of the subformulae I14a, I14b, I14c and I14e.

The preferred compounds of the subformula I16 include those of the subformulae I16a to I16h:

$R^1$—W—$Cyc^a$—$Z^2$—$Cyc^a$—$R^2$    I16a $R^1$—W—$A^2$—$CH_2CH_2$—$A^2$—$R^2$    I16b $R^1$—W—$Phe^a$—$Z^2$—$Cyc^a$—$R^2$    I16c $R^1$—W—$Phe^a$—COO—$A^2$—$R^2$    I16d $R^1$—W—$Phe^a$—$Z^2$—$Phe^a$—$R^2$    I16e $R^1$—W—$A^2$—$Z^2$—$Pyr^a$—$R^2$    I16f $R^1$—W—$A^2$—$Z^2$—Pyd—$R^2$    I16g $R^1$—W—$A^2$—$Z^2$—Dio—$R^2$    I16h.

Of these, particular preference is given to those of the subformulae I16a, I16b, I16c and I16e.

In the compounds of the formulae above and below, $R^1$ and $R^2$ are preferably unsubstituted, straight-chain alkyl, alkenyl, oxalkyl or oxalkenyl having 1 to 12 carbon atoms; $R^1$ and $R^2$ are particularly preferably unsubstituted, straight-chain alkyl having 1 to 7 carbon atoms or unsubstituted, straight-chain alkenyl having 2 to 10 carbon atoms. The alkenyl radical is preferably 1E-alkenyl, 3E-alkenyl or 4-alkenyl and particularly preferably 1E- or 3E-alkenyl. $R^2$ is secondarily preferably F, Cl, $OCF_3$, $OCHF_2$, $CF_3$, $CHF_2$, $OCHFCF_3$, $OCHFCHF_2$, $OCH_2CF_3$, $OC_2F_5$, $OC_3F_7$, OCF=CHF, $OCF_2CHFCF_3$, in particular F, $OCF_3$, $OCHF_2$, $OCHFCF_3$ or $OCHFCHF_2$.

$A^1$ and $A^2$ are preferably, independently of one another, $Phe^a$, $Cyc^a$, Che, Pyd or $Pyr^a$, particularly preferably $Phe^a$, $Cyc^a$ or Che, especially preferably $Phe^a$ or $Cyc^a$.

$A^1$ and $A^2$ are preferably, independently of one another,

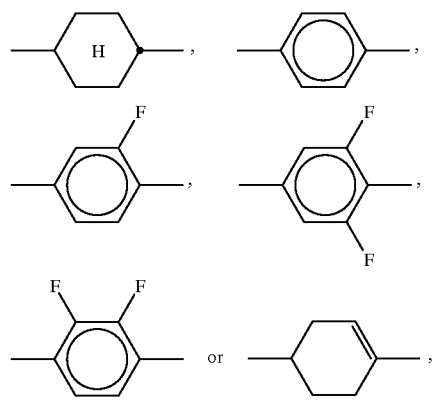

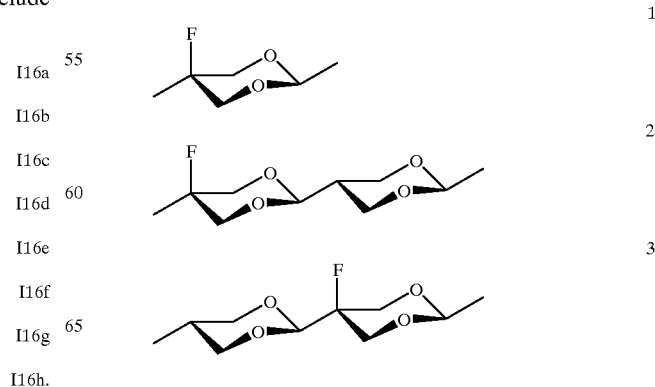

where the rings can also occur in inverted form.

If the ring $A^1$ is present more than once, these rings can have identical or different meanings. The same also applies to the ring $A^2$, and to the bridges $Z^1$ and $Z^2$.

$Z^1$, $Z^2$, $Z^3$ and $Z^4$ are preferably, independently of one another, $CH_2CH_2$ or a single bond, particularly preferably a single bond.

m and n are preferably, independently of one another, 0, 1 or 2, particularly preferably 0 or 1.

The sum $n_1+n_2+n_3+m+n$ is preferably 2 or 3, particularly preferably 2.

The sum $n_4+n_5+n_6+m+n$ is preferably 1, 2 or 3, particularly preferably 2 or 3, especially preferably 2.

The formulae 1 to 17 $^{show}$ particularly preferred meanings of the structural unit W

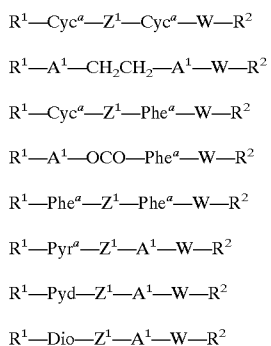

1

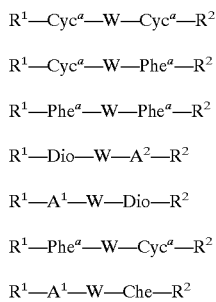

2

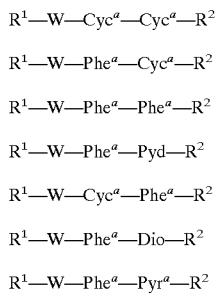

3

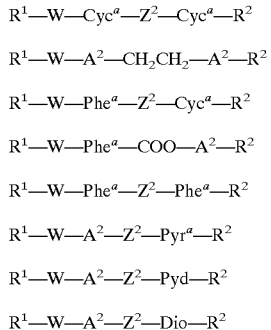

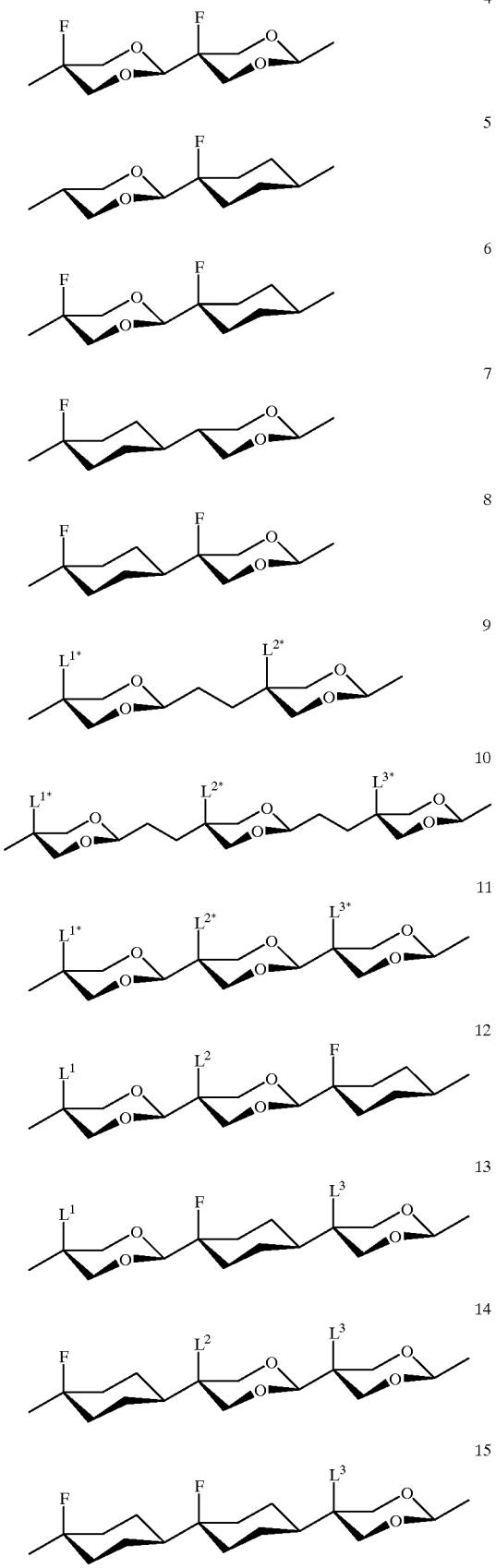

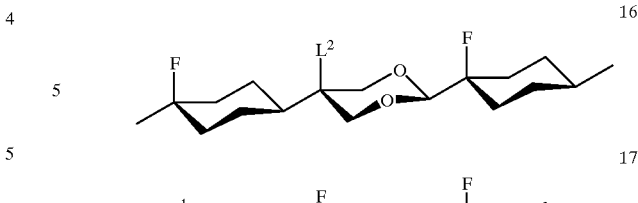

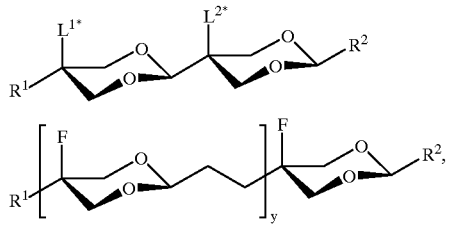

$L^1$, $L^2$ and $L^3$ are each, independently of one another, H or F. One of the radicals $L^{1*}$, $L^{2*}$ and $L^{3*}$ is F, and the other radicals $L^{1*}$, $L^{2*}$ and $L^{3*}$ are each, independently of one another, H or F. If only two of the radicals $L^{1*}$, $L^{2*}$ and $L^{3*}$ are present in a formula, i.e. $L^{1*}$ and $L^{2*}$ or $L^{1*}$ and $L^{3*}$ or $L^{2*}$ and $L^{3*}$, one of these two radicals is F and the other is H or F.

Of these structural units W, those of the formula 1 to 10 are particularly preferred.

In all compounds of the formula I, the fluorine atoms in the structural units W are in the axial position in the fluorocyclohexane or 5-fluoro-1,3-dioxane units. The other substituents are in the trans-arrangement to one another. This connection is illustrated by way of example with reference to the following preferred compounds according to the invention:

in which one of the radicals $L^{1*}$ and $L^{2*}$ is F and the other of these radicals is H or F, and y is 1 or 2, and $R^1$ and $R^2$ are as defined above.

If $R^1$ and $R^2$ are an alkyl and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, methoxy, octoxy, nonoxy, decoxy or undecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ and $R^2$ are an alkenyl radical, this can be straight-chain or branched. It is preferably straight-chain and has 2 to 10 carbon atoms. Accordingly, it is in particular vinyl, prop-1- or 2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ and $R^2$ are an alkenyl radical in which one $CH_2$ group has been replaced by —O—, this can be straight-chain or branched. It is preferably straight-chain and has 2 to 10 carbon atoms. Accordingly, it is in particular vinyloxy, prop-1- or -2-enyloxy, but-1-, -2- or -3-enyloxy, pent-1-, -2-, -3- or -4-enyloxy, hex-1-, -2-, -3-, -4- or -5-enyloxy, hept-1-, -2-, -3-, -4-, -5- or -6-enyloxy, oct-1-, -2-, -3-, -4-, -5-, -6- or -7-enyloxy, non-1-, -2-, -3-, -4-, -5-, -6-, -7- or -8-enyloxy or dec-1-, -2-, -3-, -4-, -5-, -6-, -7-, -8- or -9-enyloxy or 2-oxabut-3-enyl (vinyloxymethyl), 2-oxapent-3- or -4-enyl or 3-oxapent-4-enyl, 2-oxahex-3-, -4- or -5-enyl, 3-oxahex-4- or -5-enyl or 4-oxahex-5-enyl, 2-oxahept-3-, -4-, -5- or -6-enyl, 3-oxahept-4-, -5- or -6-enyl, 4-oxahept-5- or -6-enyl or 5-oxahept-6-enyl, 2-oxaoct-3-, -4-, -5-, -6- or -7-enyl, 3-oxaoct-4-, -5-, -6- or -7-enyl, 4-oxaoct-5-, -6- or -7-enyl, 5-oxaoct-6- or -7-enyl or 6-oxaoct-7-enyl, 2-oxanon-3-, -4-, -5-, -6-, -7- or -8-enyl, 3-oxanon-4-, -5-, -6-, -7- or -8-enyl, 4-oxanon-5-, -6-, -7- or -8-enyl, 5-oxanon-6-, -7- or -8-enyl, 6-oxanon-7- or -8-enyl or 7-oxanon-8-enyl or 2-oxadec-3-, -4-, -5-, -6-, -7-, -8- or -9-enyl, 3-oxadec-4-, -5-, -6-, -7-, -8- or -9-enyl, 4-oxadec-5-, -6-, -7-, -8- or -9-enyl, 5-oxadec-6-, -7-, -8- or -9-enyl, 6-oxadec-7-, -8- or -9-enyl, 7-oxadec-8- or -9-enyl or 8-oxadec-9-enyl, 2-oxaundec-3-, -4-, -5-, -6-, -7-, -8-, -9- or -10-enyl, 3-oxaundec-4-, -5-, -6-, -7-, -8-, -9- or -10-enyl, 4-oxaundec-5-, -6-, -7-, -8-, -9- or -10-enyl, 5-oxaundec-6-, -7-, -8-, -9- or -10-enyl, 6-oxaundec-7-, -8-, -9- or -10-enyl, 7-oxaundec-8-, -9-or -10-enyl, 8-oxaundec-9- or -10-enyl or 9-oxaundec-10-enyl.

If $R^1$ and $R^2$ are an alkyl radical in which one $CH_2$ group has been replaced by —O— and one has been replaced by —CO—, these are preferably adjacent. They thus contain an acyloxy group —CO—O—or an oxycarbonyl group —O—CO—. These are preferably straight-chain and have 2 to 6 carbon atoms. Accordingly, they are in particular acetyloxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)butyl.

If $R^1$ and $R^2$ are an alkyl or alkenyl radical which is monosubstituted by CN or $CF_3$, this radical is preferably straight-chain, and the substitution by CN or $CF_3$ is in the ω-position.

If $R^1$ and $R^2$ are an alkyl or alkenyl radical which is at least monosubstituted by halogen, this radical is preferably straight-chain, and halogen is preferably F or Cl. In the case of multiple substitution, halogen is preferably F. The resultant radicals also include perfluorinated radicals. In the case of monosubstitution, the fluorine or chlorine substituent can be in any desired position, but is preferably in the ω-position.

Compounds of the formula I having branched wing groups $R^1$ and $R^2$ may occasionally be of importance owing to better solubility in the conventional liquid-crystalline base materials, but in particular as chiral dopants if they are optically active. Smectic compounds of this type are suitable as components of ferro-electric materials.

Compounds of the formula I having $S_A$ phases are suitable, for example, for thermally addressed displays.

Branched groups of this type generally contain not more than one chain branch. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy.

The formula I also covers the raceLTnates of these canpounds and the optical antipodes, and mixtures thereof.

Of these compounds of the formula I and of the subformulae, preference is given to those in which at least one of the radicals present therein has one of the preferred meanings indicated.

Some very particularly preferred subgeneric groups of compounds of the formula I according to the invention are those of the subformulae Ia1 to Ih6:

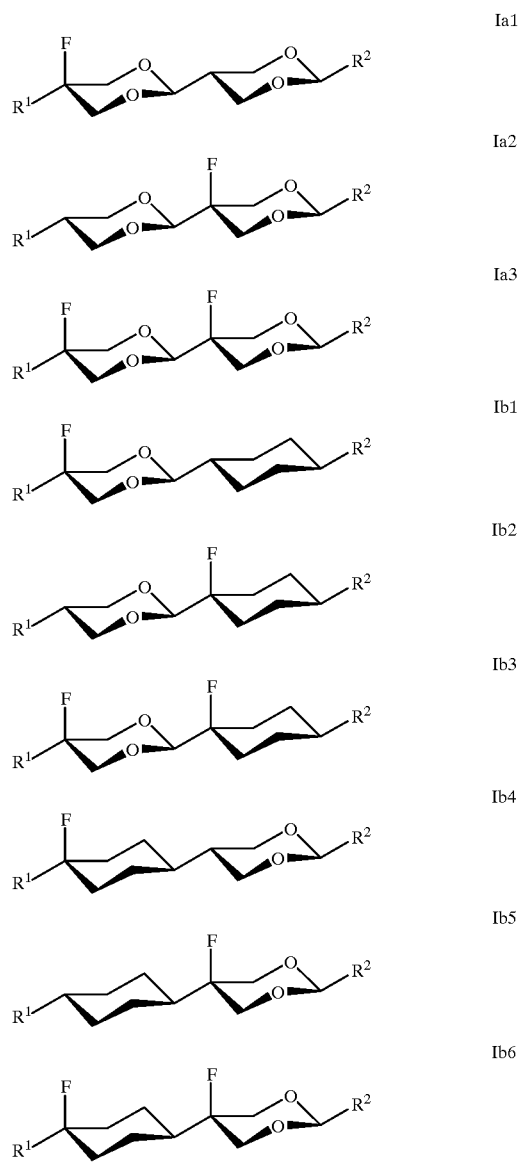

Ic1
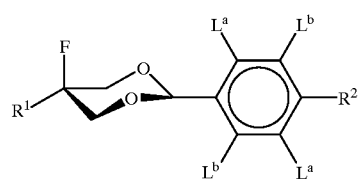
Ic2
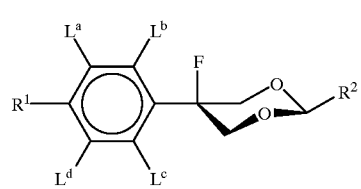
Id1
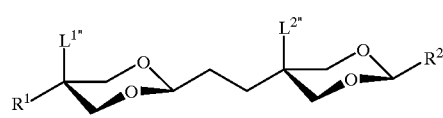
Id2
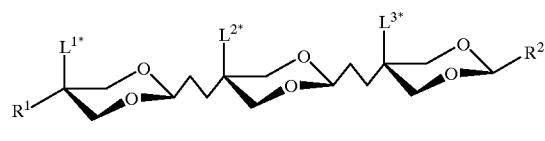
Ie
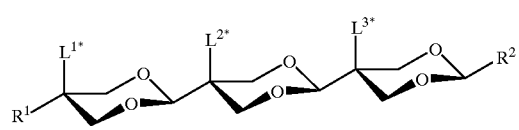
If1
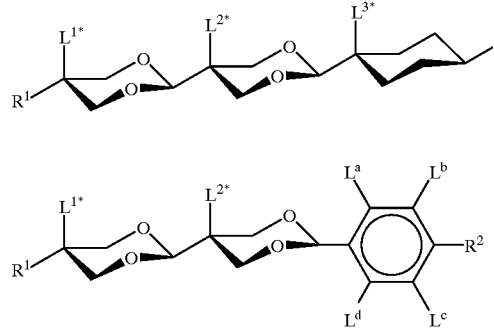
If2
If3
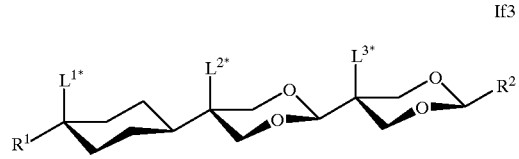
If4
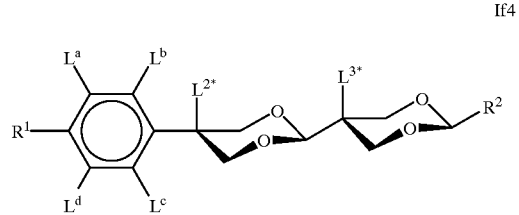
Ig1
Ig2
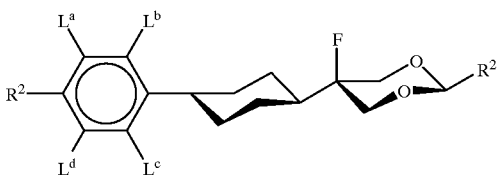
Ig3
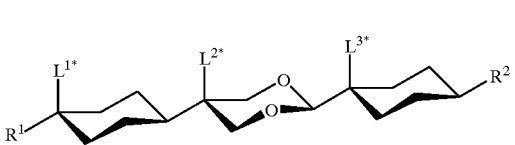
Ig4
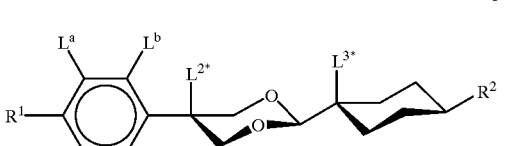
Ig5
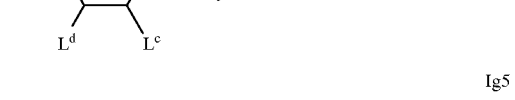
Ig6
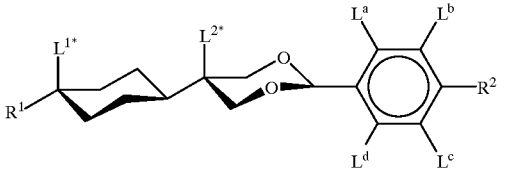
Ig7
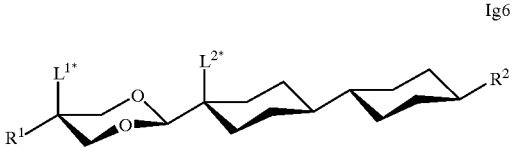
Ih1
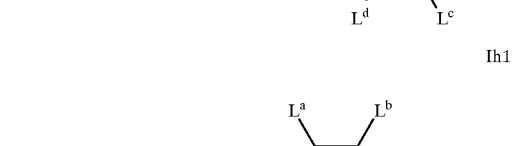

-continued

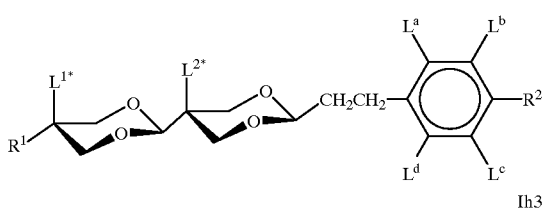
Ih2

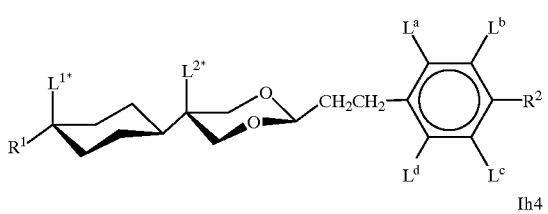
Ih3

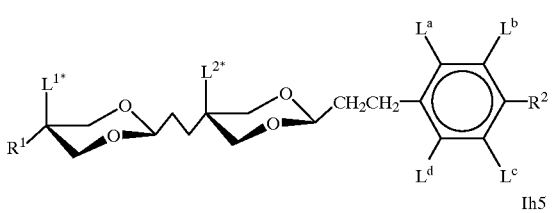
Ih4

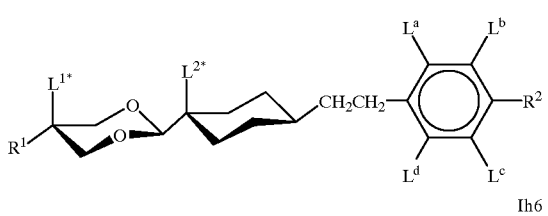
Ih5

Ih6

$L^1$, $L^2$, $L^3$, $L^a$, $L^b$, $L^c$ and $L^d$ are each, independently of one another, H or F. One of the radicals $L^{1*}$, $L^{2*}$ and $L^{3*}$ is F, and the other radicals $L^{1*}$, $L^{2*}$ and $L^{3*}$ are each, independently of one another, H or F. If only two of the radicals $L^{1*}$, $L^{2*}$ and $L^{3*}$ are present in a formula, i.e. $L^{1*}$ and $L^{2*}$ or $L^{1*}$ and $L^{3*}$ or $L^{2*}$ and $L^{3*}$, one of these two radicals is F and the other is H or F.

Of the compounds of the formulae Ia1 to Ih6, preference is given to those of the formulae Ia1 to Ia3, Ib1 to Ib6, Id1 and Id2. Particularly preferred compounds of the formulae Ia1 to Ia3, Ib1 to Ib6, Id1 and Id2 are those in which $R^1$ and $R^2$ are each, independently of one another, an alkyl radical having 1 to 12 carbon atoms, preferably a straight-chain, unsubstituted alkyl radical having 1 to 7 carbon atoms, or an alkenyl radical having 2 to 12 carbon atoms, preferably a straight-chain, unsubstituted alkenyl radical having 2 to 10 carbon atoms. Of these alkenyl radicals, particular preference is given to the 1E-alkenyl and 3E-alkenyl radicals.

The compounds of the formula I are prepared by methods known per se, as described in the literature (for example in the standard works, such as Houben-Weyl, Methoden der Organischen Chemie, Georg-Thieme-Verlag, Stuttgart), to be precise under reaction conditions which are known and suitable for said reactions.

Use can also be made here of variants which are known per se, but are not mentioned here in greater detail.

The starting materials are either known or can be prepared by known methods. If desired, they can also be formed in situ by not isolating them from the reaction mixture, instead immediately converting them into the compounds of the formula I.

The compounds according to the invention can be prepared, for example, in accordance with the following reaction schemes:

Scheme 1

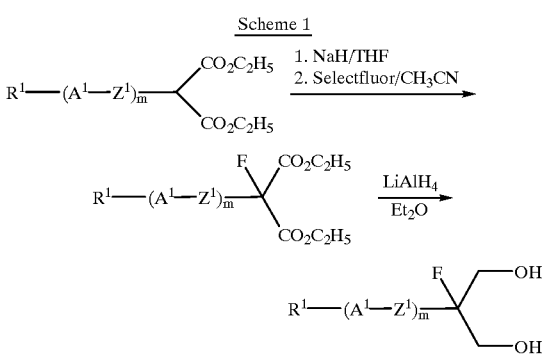

$R^1$—$(A^1$—$Z^1)_m$— in the reaction described in this scheme is preferably alkyl, aryl, 4-alkoxycyclohexyl or 4-arylcyclohexyl.

Scheme 2

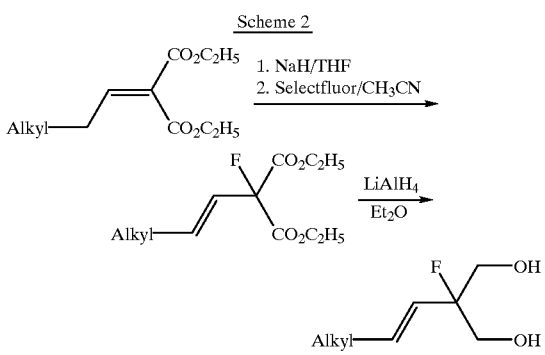

Scheme 3

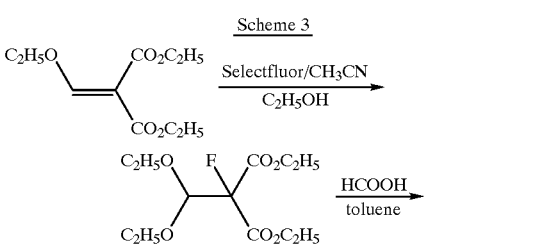

Scheme 4
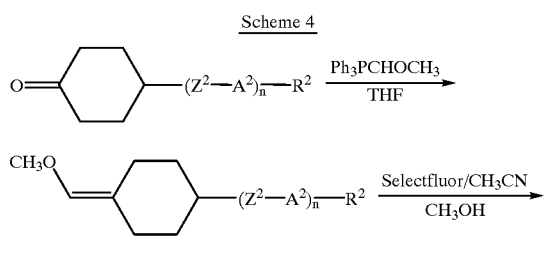
—(Z²—A²)ₙ—R² in the reaction described in this scheme is preferably alkyl, alkenyl or aryl. Scheme 5
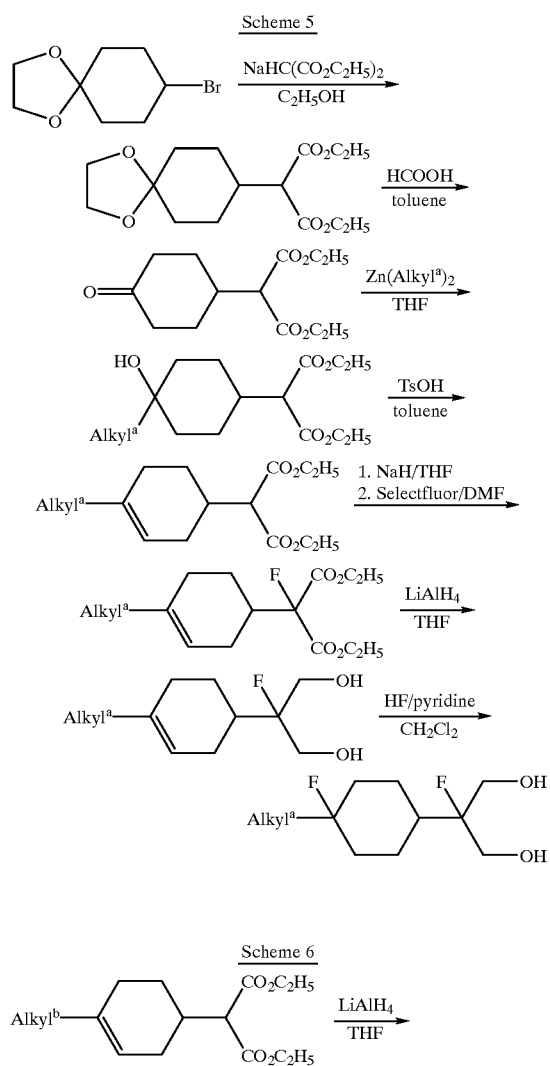
-continued
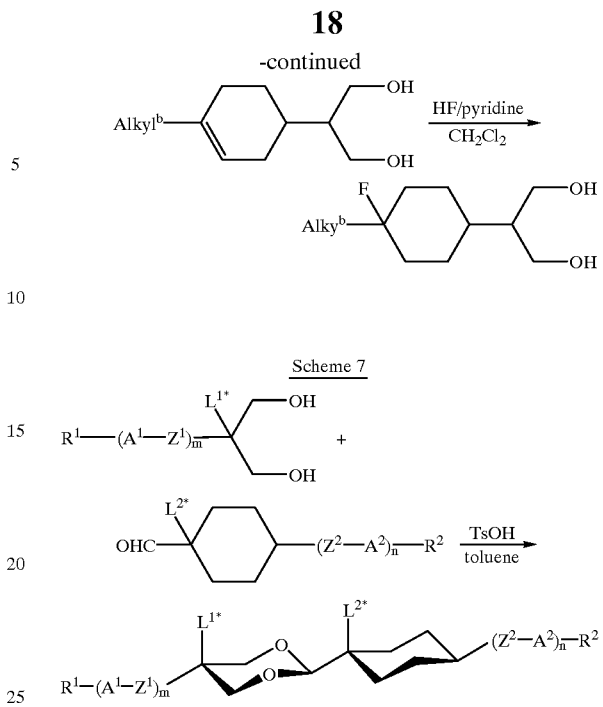
One of the radicals $L^{1*}$ and $L^{2*}$ is F, and the other is H or F.
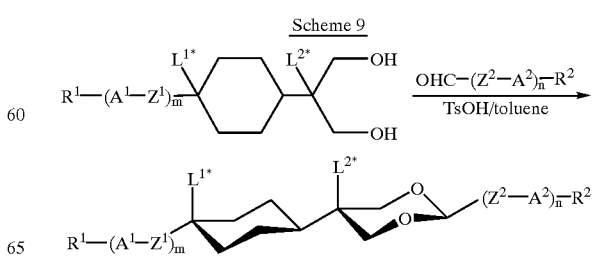

One of the radicals $L^{1*}$ and $L^{2*}$ is F, and the other is H or F.
One of the radicals $L^{1*}$ and $L^{2*}$ is F, and the other is H or F.
Scheme 10
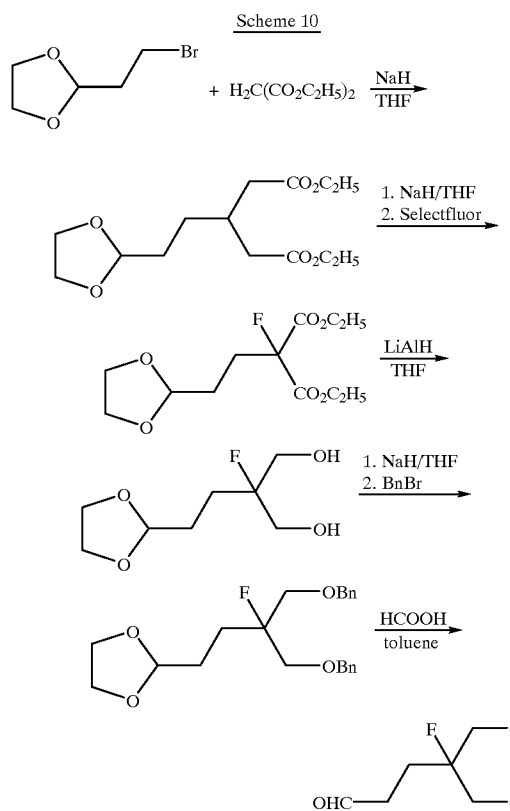
Scheme 12
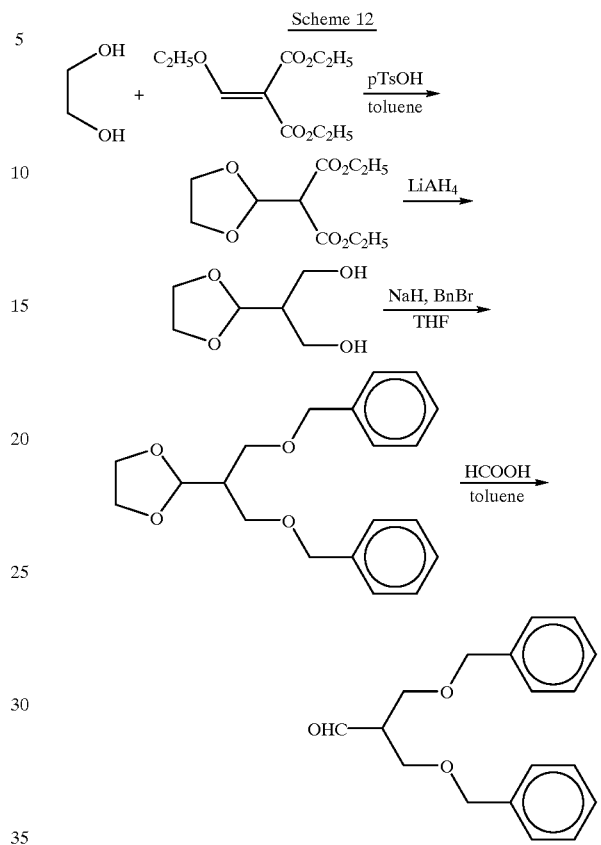
Scheme 11
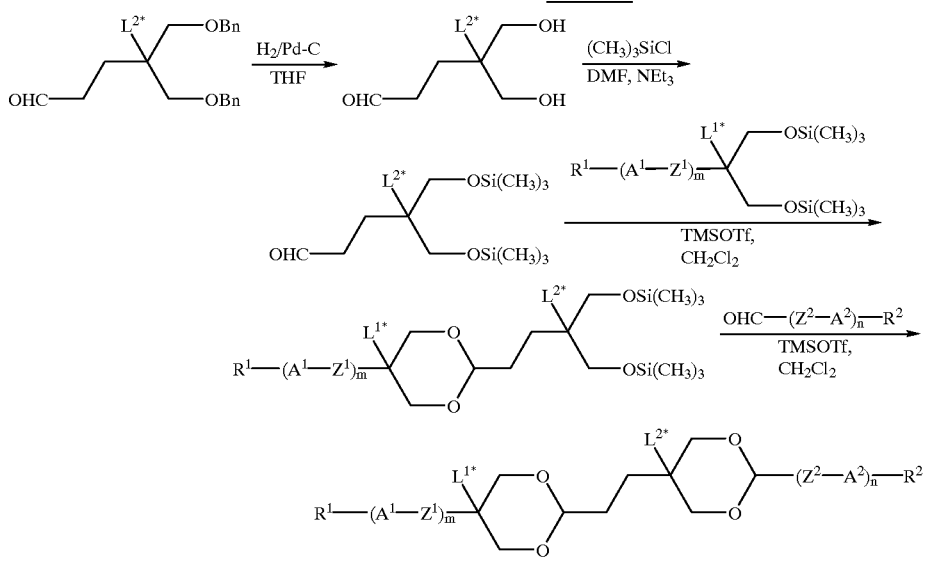

By reacting
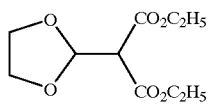   5
with NaH/THF and Selectfluor/DMF, it is also possible to prepare the compound OHC—CHF—$(CH_2OCH_2C_6H_5)_2$.
Scheme 13
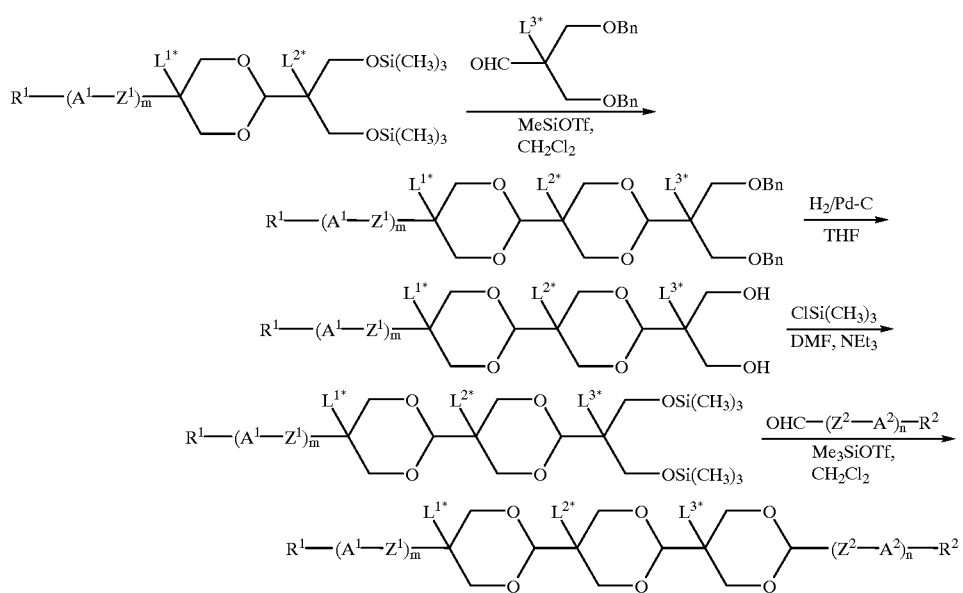
One of the radicals $L^{1*}$, $L^{2*}$ and $L^{3*}$ is F, and the other radicals $L^{1*}$, $L^{2*}$ and $L^{3*}$ are each, independently of one another, H or F.
Preferred compounds of the formula I are prepared as follows:
Scheme 14
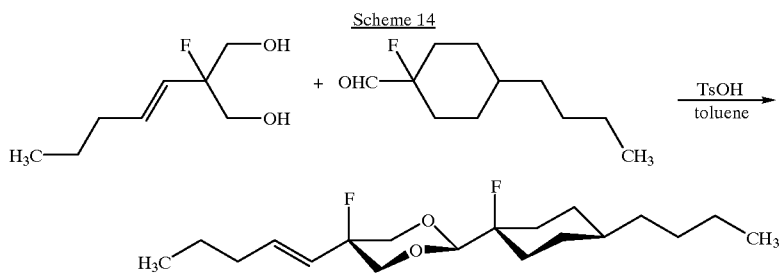

Scheme 15

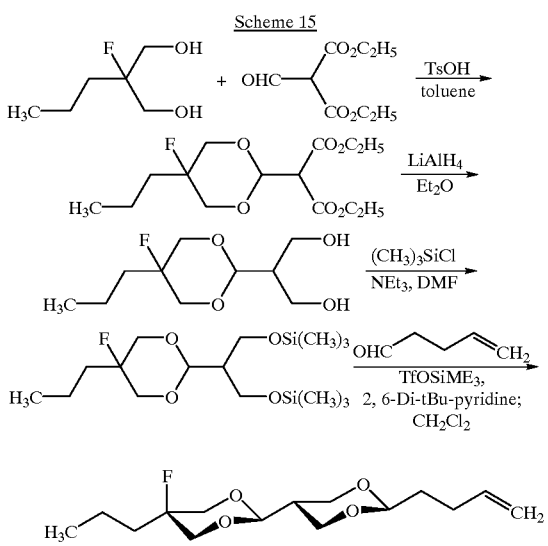

Scheme 16

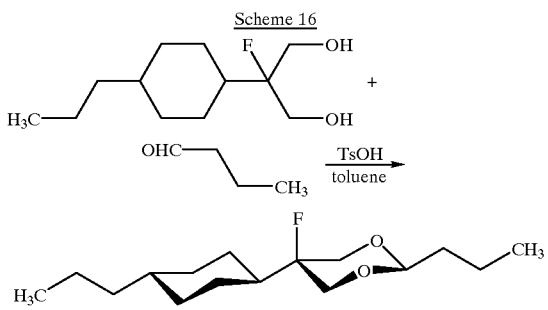

The liquid-crystalline media according to the invention preferably comprise from 2 to 40, in particular from 4 to 30, components as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohaxenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-di-cyclohexylethanes, 1-phenyl-2-cyclohexylethanes, 1-cyclohexyl-2-(4-phenylcyclohexyl)ethanes, 1-cyclohexyl-2-bi-phenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'—A—E—R" | 1 |
| R'—A—COO—E—R" | 2 |
| R'—A—OOC—E—R" | 3 |
| R'—A—CH$_2$CH$_2$—E—R" | 4 |
| R'—A—C≡C—E—R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyridine-2,5-diyl or pyridine-2,5-diyl, Dio is 1,3-dioxane-2,5-diyl and G is 2-(trans-1,4-cyclohexyl)ethyl, pyridine-2,5-diyl, pyridine-2,5-diyl or 1,3-dioxane-2,5-diyl.

One of the radicals A and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which A and E are selected from the group consisting of Cyc, Phe and Pyr and simultaneously one or more components selected from the compounds of the formulae 1, 2, 3, 4 and 5 in which one of the radicals A and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals A and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+l)}$F$_k$Cl$_l$, where i is 0 or 1, and k+l is 1, 2 or 3; the compounds in which R" has this meaning are labelled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invention are preferably Group A: from 0 to 90%, preferably from 10 to 90%, in particular from 30 to 90%

Group B: from 0 to 80%, preferably from 10 to 80%, in particular from 10 to 65%

Group C: from 0 to 80%, preferably from 5 to 80%, in particular from 5 to 50%, the sum of the proportions by weight of the group A and/or B and/or C compounds present in the particular media according to the invention preferably being from 5 to 90% and in particular from 10 to 90%.

The media according to the invention preferably comprise from 1 to 40%, particularly preferably from 5 to 30%, of compounds according to the invention. Further preferred media are those which comprise more than 40%, in particular from 45 to 90%, of compounds according to the invention. The media preferably comprise three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the alignment of the nematic phases.

The entire disclosure of all applications, patents and publications, cited above and below, and of corresponding German application No. 197 23 277.9, filed Jun. 4, 1997 is hereby incorporated by reference.

EXAMPLES

In the present application and in the examples below, the structures of the liquid-crystal compounds are indicated by acronyms, the transformation into chemical formulae taking place as in Tables A and B below. All the radicals $C_nH_{2n+1}$ and $C_mH_{2m+1}$ are straight-chain alkyl radicals containing n or m carbon atoms respectively. The coding in Table B is self-evident. In Table A, only the acronym for the parent structure is given. In individual cases, the acronym for the parent structure is followed, separated by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
| --- | --- | --- | --- | --- |
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | COOC$_m$H$_{2m+1}$ | H | H |

TABLE A

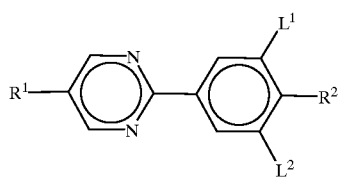

PYP

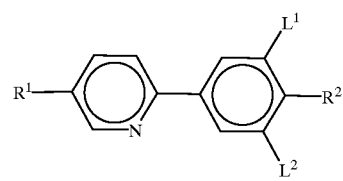

PYRP

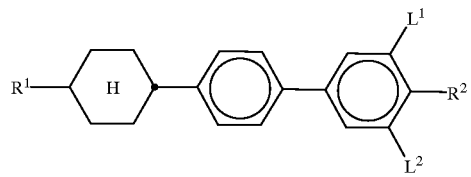

BCH

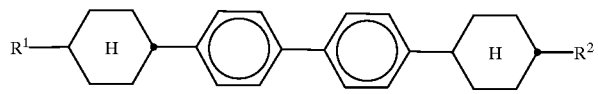

CBC

TABLE A-continued
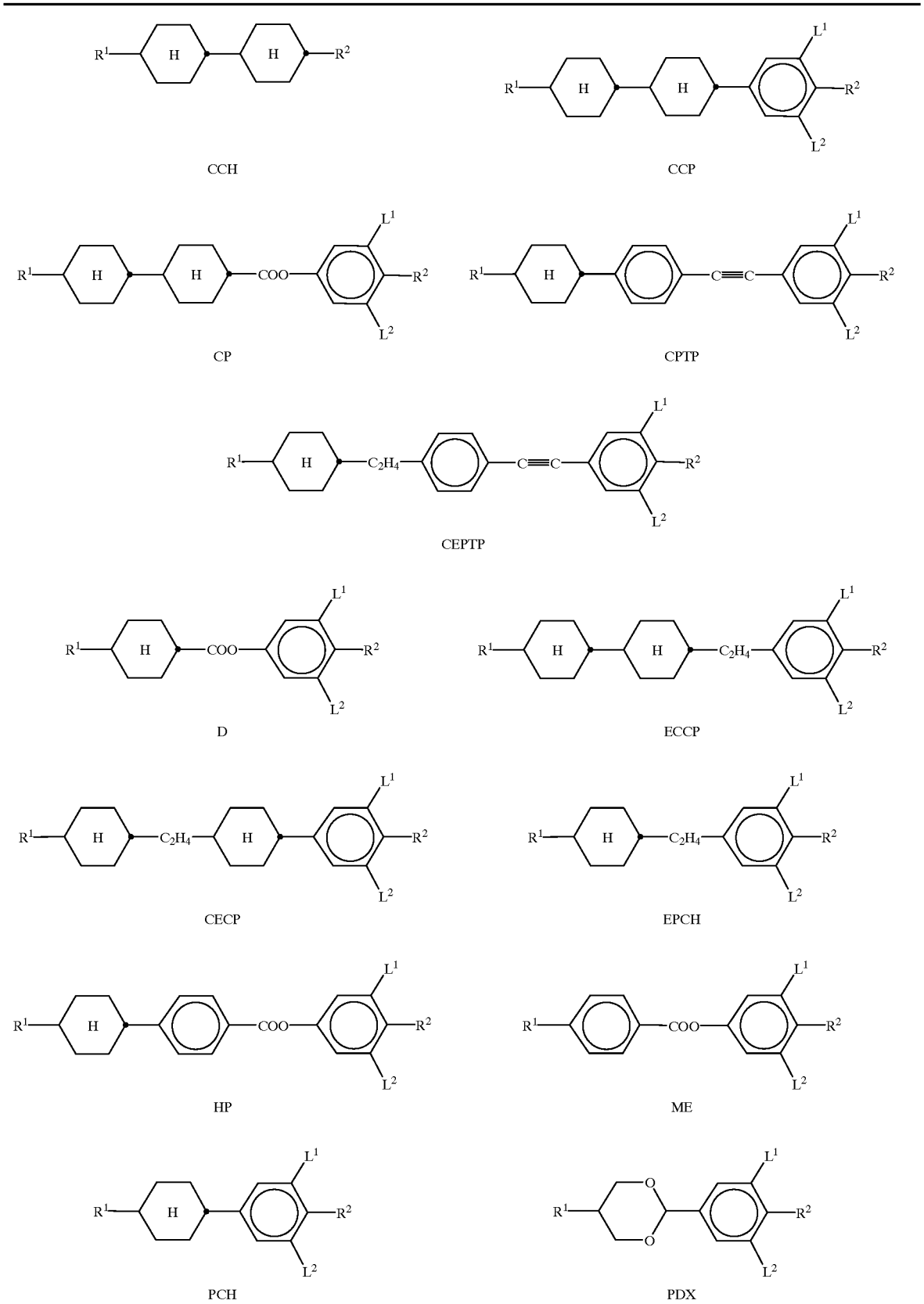

TABLE A-continued
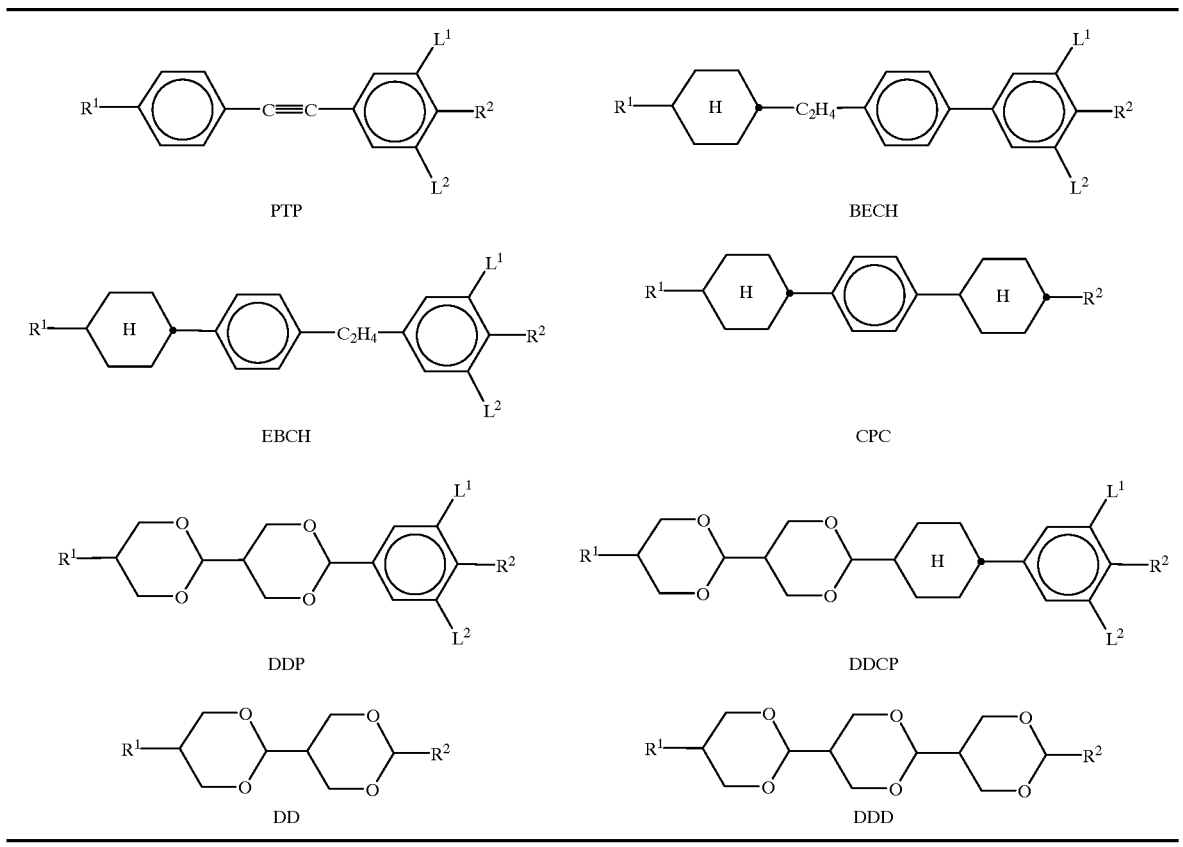
TABLE B
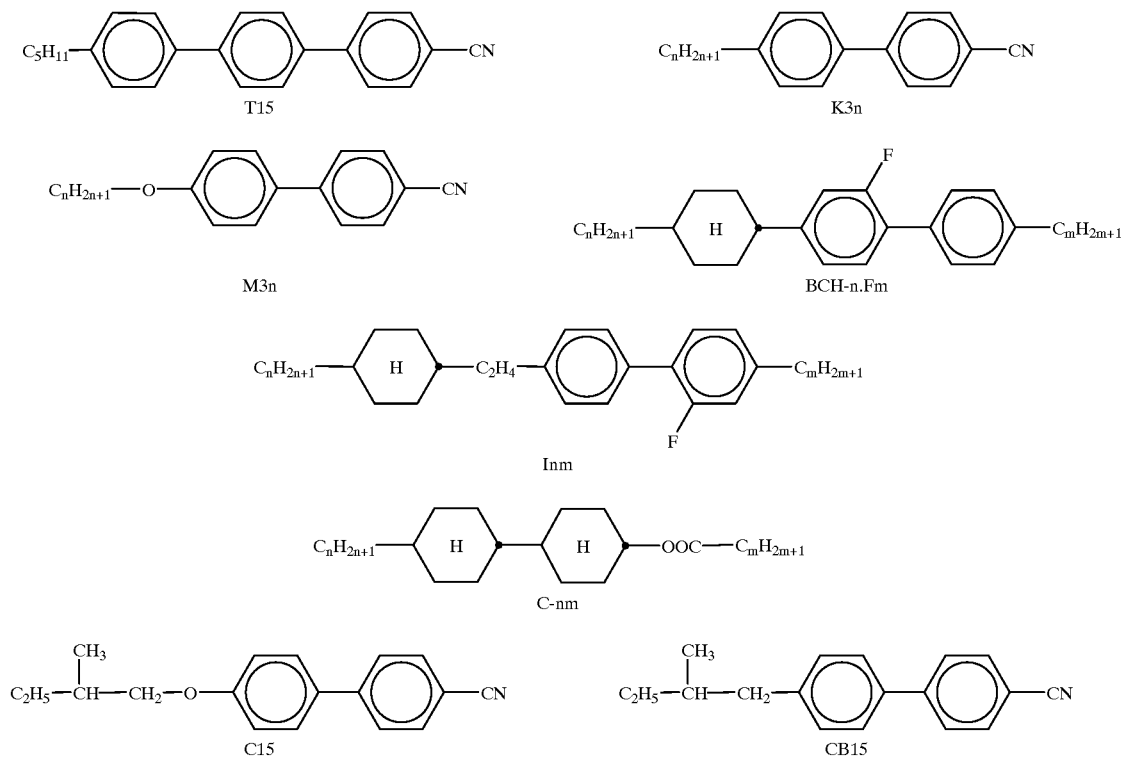

TABLE B-continued
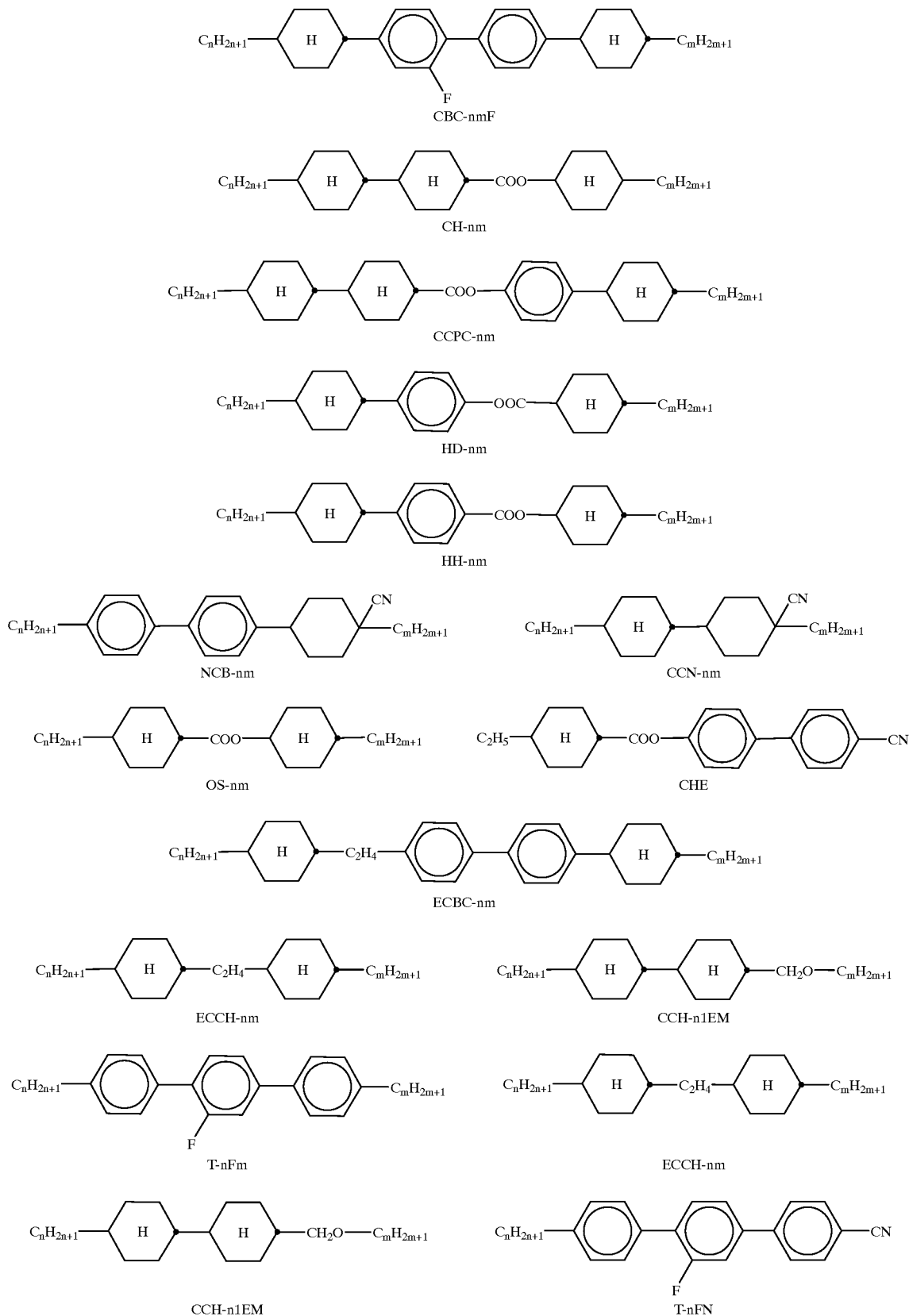

TABLE B-continued

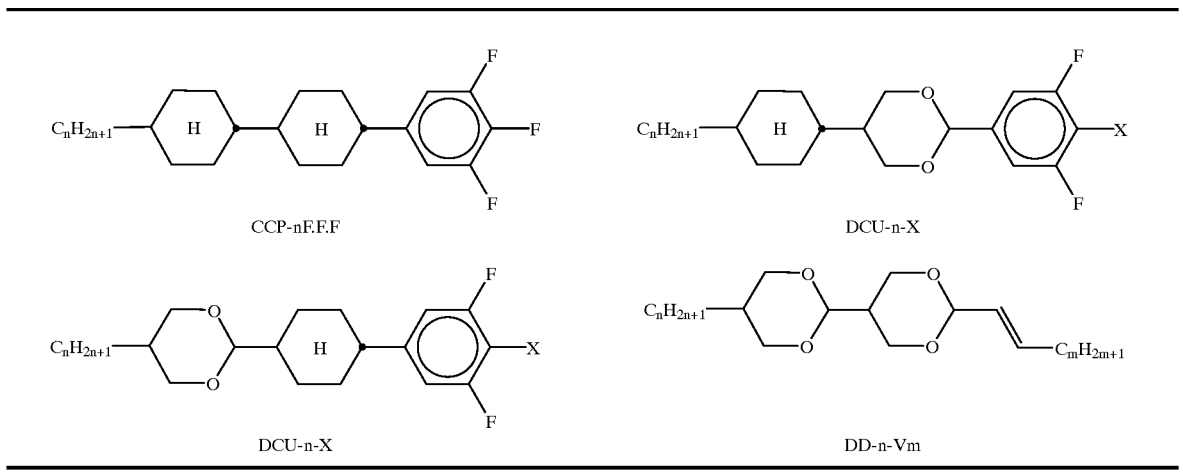

The examples below are intended to illustrate the invention without representing a limitation. Above and below, per cent data are per cent by weight. All temperatures are given in degrees Celsius. b.p. denotes boiling point, m.p.=melting point, cl.p.=clearing point. Furthermore, C=crystalline state, N=nematic phase, S=smectic phase and I=isotropic phase. The numbers between these symbols indicate the conversion temperature in degrees Celsius. Δn denotes optical anisotropy (589 nm, 20° C.), and the viscosity (mm²/sec) was determined at 20° C.

"Conventional work-up" means that water is added if necessary, the mixture is extracted with dichloromethane, diethyl ether, n-pentane or toluene, the organic phase is separated off, dried and evaporated, and the product is purified by distillation under reduced pressure or crystallization and/or chromatography. The following abbreviations are used:

| | |
|---|---|
| NaH | sodium hydride |
| TsOH | p-toluenesulphonic acid (also abbreviated to pTsOH) |
| BnBr | benzyl bromide |
| Pd/C | palladium on activated charcoal |
| CH$_3$CN | acetonitrile |
| Et$_2$O | diethyl ether |
| tBu | tert-butyl |
| ClSi (CH$_3$)$_3$ | chlorotrimethylsilane |
| THF | tetrahydrofuran |
| LiAlH$_4$ | lithium aluminium hydride |
| NEt$_3$ | triethylamine |
| DMF | N,N-dimethylformamide |
| Me$_3$SiOTf | trimethylsilyl trifluoromethanesulphonate (also abbreviated to TMSOTf) |
| Selectfluor | N-fluoro-N-chloromethyltriethylenediamine bis(tetrafluoroborate) |
| Ph$_3$PCHOCH$_3$ | methoxymethylenetriphenylphosphane |

Example 1

Step 1

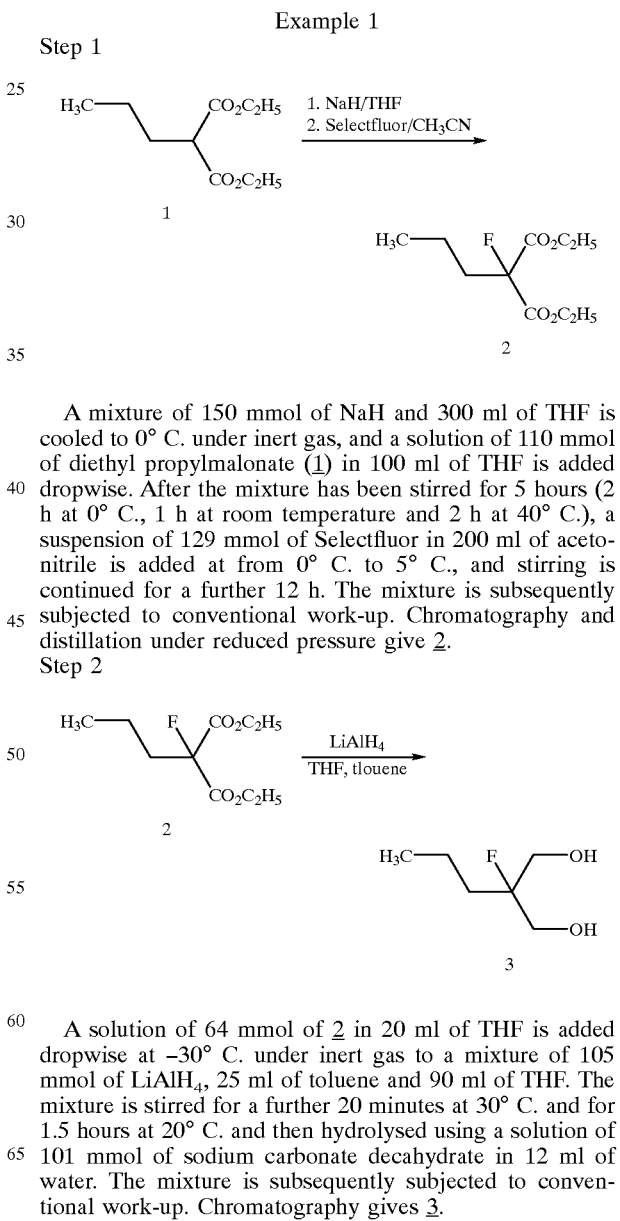

A mixture of 150 mmol of NaH and 300 ml of THF is cooled to 0° C. under inert gas, and a solution of 110 mmol of diethyl propylmalonate (1) in 100 ml of THF is added dropwise. After the mixture has been stirred for 5 hours (2 h at 0° C., 1 h at room temperature and 2 h at 40° C.), a suspension of 129 mmol of Selectfluor in 200 ml of acetonitrile is added at from 0° C. to 5° C., and stirring is continued for a further 12 h. The mixture is subsequently subjected to conventional work-up. Chromatography and distillation under reduced pressure give 2.

Step 2

A solution of 64 mmol of 2 in 20 ml of THF is added dropwise at −30° C. under inert gas to a mixture of 105 mmol of LiAlH$_4$, 25 ml of toluene and 90 ml of THF. The mixture is stirred for a further 20 minutes at 30° C. and for 1.5 hours at 20° C. and then hydrolysed using a solution of 101 mmol of sodium carbonate decahydrate in 12 ml of water. The mixture is subsequently subjected to conventional work-up. Chromatography gives 3.

Step 3

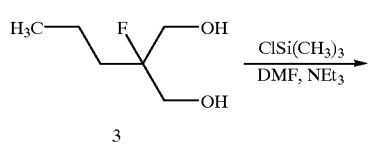

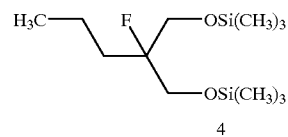

80 mmol of chlorotrimethylsilane are added dropwise under inert gas to a mixture of 29 mmol of 3, 160 mmol of triethylamine and 50 ml of N,N-dimethylformamide at such a rate that the temperature does not rise above 30° C. The mixture is stirred at room temperature for a further 2 hours, 100 ml of n-pentane are added, and the mixture is stirred for a further 5 minutes and subjected to a conventional work-up. Distillation under reduced pressure gives 4.

Step 4

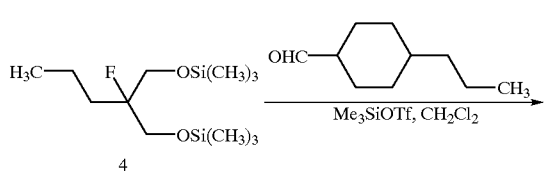

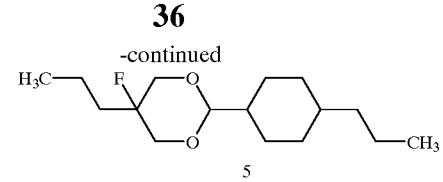

25 mmol of trans-4-n-propylcyclohexane aldehyde in 20 ml of $CH_2Cl_2$ are added dropwise at −70° C. under inert gas to a mixture of 20 mmol of 4, 80 ml of $CH_2Cl_2$ and 3 mmol of trimethylsilyl trifluoromethanesulphonate. After the mixture has been stirred at −70° C. for 2 hours, 30 mmol of pyridine are added dropwise, the mixture is slowly warmed to room temperature, 100 ml of saturated $NaHCO_3$ solution are added, the mixture is stirred for a further 0.25 h and then subjected to conventional work-up. Chromatography and recrystallization from hexane give 5; C 112 I; $\Delta\epsilon=-4.3$; $\Delta n=+0.036$.

The following compounds of the formula I $$R^1—(A^1—Z^1)_m—W—(Z^2—A^2)_n—R^2 \qquad (I)$$

are prepared analogously to the above Example 1:

Examples 2–97

| No. | $R^1$ | $—(A^1—Z^1)_m—W—(Z^2—A^2)_n—$ | $R^2$ |
|---|---|---|---|
| 2 | $C_2H_5$ | 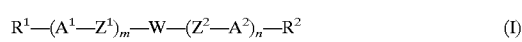 | $C_2H_5$ |
| 3 | $C_2H_5$ | | n-$C_3H_7$ |
| 4 | n-$C_3H_7$ | | n-$C_5H_{11}$ |
| 5 | $H_3COC_2H_4CH_2$ | | n-$C_3H_7$ |
| 6 | n-$C_3H_7$ | | $CH=CH_2$ |

-continued

| No. | R$^1$ | —(A$^1$—Z$^1$)$_m$—W—(Z$^2$—A$^2$)$_n$— | R$^2$ |
|---|---|---|---|
| 7 | n-C$_3$H$_7$ | [structure: difluoro-free bicyclic pyran with F on left ring] | CH=CH—CH$_3$ |
| 8 | C$_2$H$_5$ | [structure] | CH=CH—C$_2$H$_5$ |
| 9 | C$_2$H$_5$ | [structure] | C$_2$H$_4$—CH=CH$_2$ |
| 10 | C$_2$H$_5$ | [structure] | CH=CH—CH$_2$—C$_2$H$_5$ |
| 11 | C$_2$H$_5$ | [structure with F on right ring] | C$_2$H$_5$ |
| 12 | n-C$_3$H$_7$ | [structure] | n-C$_3$H$_7$ |
| 13 | C$_2$H$_5$ | [structure] | CH=CH$_2$ |
| 14 | H$_2$C=CH | [structure] | CH=CH$_2$ |
| 15 | H$_2$C=CH | [structure] | n-C$_3$H$_7$ |
| 16 | C$_2$H$_5$ | [structure with F on both rings] | C$_2$H$_5$ |
| 17 | n-C$_3$H$_7$ | [structure] | n-C$_3$H$_7$ |
| 18 | C$_2$H$_5$ | [structure] | CH=CH$_2$ |

-continued

| No. | R¹ | —(A¹—Z¹)ₘ—W—(Z²—A²)ₙ— | R² |
|---|---|---|---|
| 19 | H₂C=CH | | CH=CH₂ |
| 20 | H₂C=CH | | n-C₃H₇ |
| 21 | C₂H₅ | | C₂H₅ |
| 22 | n-C₃H₇ | | n-C₅H₁₁ |
| 23 | C₂H₅ | | C₂H₅ |
| 24 | n-C₃H₇ | | n-C₃H₇ |
| 25 | n-C₃H₇ | | n-C₅H₁₁ |
| 26 | C₂H₅ | | C₂H₅ |
| 27 | n-C₃H₇ | | n-C₃H₇ |
| 28 | n-C₃H₇ | | CH=CH₂ |
| 29 | n-C₃H₇ | | n-C₃H₇ |

-continued

| No. | R¹ | —(A¹—Z¹)ₘ—W—(Z²—A²)ₙ— | R² |
|---|---|---|---|
| 30 | n-C₃H₇ | | n-C₅H₁₁ |
| 31 | n-C₅H₁₁ | | n-C₃H₇ |
| 32 | n-C₃H₇ | | n-C₃H₇ |
| | | C 97 S$_B$(97) I; Δε = −4.2; Δn = +0.025 | |
| 33 | n-C₃H₇ | | n-C₅H₁₁ |
| 34 | n-C₅H₁₁ | | n-C₃H₇ |
| 35 | n-C₃H₇ | | n-C₃H₇ |
| 36 | n-C₃H₇ | | n-C₅H₁₁ |
| 37 | n-C₅H₁₁ | | n-C₃H₇ |
| 38 | n-C₃H₇ | | F |
| 39 | n-C₅H₁₁ | | CN |

| No. | R¹ | —(A¹—Z¹)ₘ—W—(Z²—A²)ₙ— | R² |
|---|---|---|---|
| 40 | n-C₃H₇ | | OCF₃ |
| 41 | C₂H₅ | | n-C₃H₇ |
| 42 | C₂H₅ | | n-C₃H₇ |
| 43 | n-C₃H₇ | | n-C₃H₇ |
| 44 | C₂H₅ | | n-C₃H₇ |
| 45 | n-C₃H₇ | | n-C₃H₇ |
| 46 | n-C₃H₇ | | n-C₃H₇ |
| 47 | C₂H₅ | | CH=CH₂ |
| 48 | H₂C=CH | | C₂H₅ |
| 49 | H₂C=CH | | CH=CH₂ |
| 50 | C₂H₅ | | n-C₃H₇ |

-continued

| No. | R¹ | —(A¹—Z¹)ₘ—W—(Z²—A²)ₙ— | R² |
|---|---|---|---|
| 51 | C₂H₅ | | n-C₃H₇ |
| 52 | C₂H₅ | | n-C₃H₇ |
| 53 | C₂H₅ | | n-C₃H₇ |
| 54 | C₂H₅ | | n-C₃H₇ |
| 55 | C₂H₅ | | n-C₃H₇ |
| 56 | n-C₃H₇ | | n-C₃H₇ |
| 57 | H₂C=CH | | n-C₃H₇ |
| 58 | C₂H₅ | | OCF₃ |
| 59 | n-C₃H₇ | | n-C₃H₇ |
| 60 | H₂C=CH | | n-C₃H₇ |
| 61 | C₂H₅ | | OCF₃ |

| No. | R¹ | —(A¹—Z¹)ₘ—W—(Z²—A²)ₙ— | R² |
|---|---|---|---|
| 62 | n-C₃H₇ | | n-C₃H₇ |
| 63 | H₂C=CH | | n-C₃H₇ |
| 64 | C₂H₅ | | OCF₃ |
| 65 | n-C₃H₇ | | n-C₃H₇ |
| 66 | C₂H₅ | | n-C₃H₇ |
| 67 | C₂H₅ | | C₂H₅ |
| 68 | n-C₃H₇ | | n-C₃H₇ |
| 69 | C₂H₅ | | n-C₃H₇ |
| 70 | C₂H₅ | | C₂H₅ |
| 71 | n-C₃H₇ | | n-C₃H₇ |
| 72 | C₂H₅ | | n-C₃H₇ |

-continued

| No. | R¹ | —(A¹—Z¹)ₘ—W—(Z²—A²)ₙ— | R² |
|---|---|---|---|
| 73 | $C_2H_5$ | | $C_2H_5$ |
| 74 | n-$C_3H_7$ | | n-$C_3H_7$ |
| 75 | $C_2H_5$ | | $C_2H_5$ |
| 76 | n-$C_3H_7$ | C 109 S$_B$ > 200 decomp. | n-$C_3H_7$ |
| 77 | $C_2H_5$ | | n-$C_3H_7$ |
| 78 | $C_2H_5$ | | $C_2H_5$ |
| 79 | n-$C_3H_7$ | | n-$C_3H_7$ |
| 80 | $C_2H_5$ | | n-$C_3H_7$ |
| 81 | $C_2H_5$ | | $C_2H_5$ |
| 82 | n-$C_3H_7$ | | n-$C_3H_7$ |
| 83 | $C_2H_5$ | | n-$C_3H_7$ |

-continued

| No. | R¹ | —(A¹—Z¹)ₘ—W—(Z²—A²)ₙ— | R² |
|---|---|---|---|
| 84 | C₂H₅ | | C₂H₅ |
| 85 | n-C₃H₇ | | n-C₃H₇ |
| 86 | C₂H₅ | | F |
| 87 | n-C₃H₇ | | n-C₃H₇ |
| 88 | C₂H₅ | | OCF₃ |
| 89 | n-C₃H₇ | | n-C₃H₇ |
| 90 | C₂H₅ | | CN |
| 91 | n-C₃H₇ | | CF₃ |
| 92 | n-C₃H₇ | | F |
| 93 | n-C₃H₇ | | OCF₃ |

-continued

| No. | R¹ | —(A¹—Z¹)ₘ—W—(Z²—A²)ₙ— | R² |
|---|---|---|---|
| 94 | n-C₃H₇ |  | OCF₃ |
| 95 | n-C₃H₇ |  | OCF₃ |
| 96 | n-C₃H₇ |  | OCF₃ |
| 97 | n-C₃H₇ |  | F |

We claim:

1. A 1,3-dioxane compound having axial fluorine substitution, of the formula I $$R^1-(A^1-Z^1)_m-W-(Z^2-A^2)_n-R^2 \quad (I)$$

in which

W is

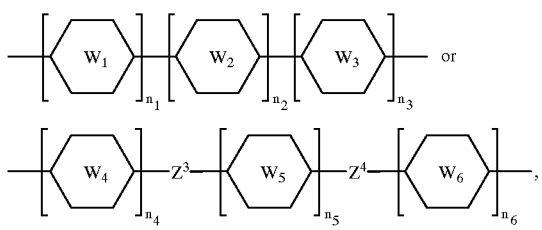

where

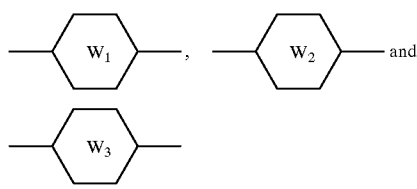

are each, independently of one another,

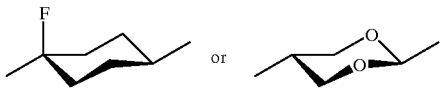

$n_1$, $n_2$ and $n_3$ are each, independently of one another, 0 or 1, provided that one of the groups

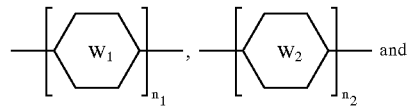

must be and another of these groups must simultaneously be

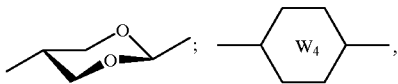

-continued

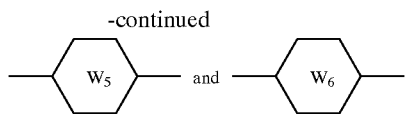

are each, independently of one another,

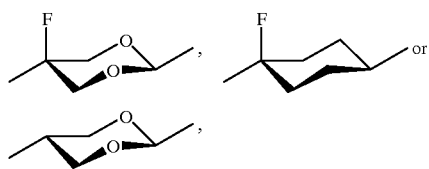

$n_4$, $n_5$ and $n_6$ are each, independently of one another, 0 or 1,
provided that one of the groups

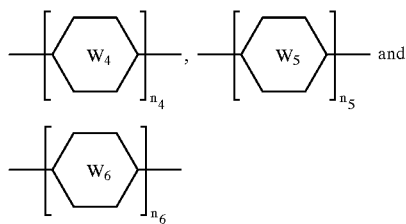

must be

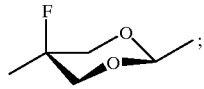

$R^1$ and $R^2$ are each, independently of one another,
 an alkyl or alkenyl radical having 1 to 12 carbon atoms which is unsubstituted, monosubstituted by CN or $CF_3$ or at least monosubstituted by halogen, where one or more $CH_2$ groups in these radicals are optionally replaced, independently of one another, by —O—, —S—, —CO—, —CO—O—, —O—CO— or —O—CO—O— in such a way that hetero atoms are not linked directly to one another,
$R^2$ is alternatively F, Cl or CN;
$A^1$ and $A^2$ are each, independently of one another,
 a) a trans-1,4-cyclohexylene radical in which, in addition, one or more non-adjacent $CH_2$ groups are optionally replaced by —O— and/or —S—,
 b) a 1,4-cyclohexenylene radical,
 c) a 1,4-phenylene radical, in which, in addition, one or two CH groups may be replaced by N, or
 d) a radical selected from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl,
 where the radicals a), b) and c) are optionally substituted by CN or F;
$Z^1$, $Z^2$, $Z^3$ and $Z^4$ are each, independently of one another,
—CO—O—, —O—CO—, —CH$_2$O—, —OCH$_2$—, —CH$_2$CH$_2$—, —CH=CH—, —C≡C— or a single bond; and m and n are each, independently of one another, 0, 1, 2 or 3;
 provided that $n_1+n_2+n_3+m+n=2$, 3 or 4, and $n_4+n_5+n_6+m+n=1$, 2, 3 or 4.

2. A 1,3-dioxane compound of the formula I according to claim 1, wherein $n_1+n_2+n_3+m+n=2$ or 3, and $n_4+n_5+n_6+m+n=2$ or 3.

3. A 1,3-dioxane compound of the formula I according to claim 1, wherein $R^1$ and $R^2$ are each, independently of one another, unsubstituted, straight-chain alkyl or 1E- or 3E-alkenyl having 1 to 12 carbon atoms.

4. A 1,3-dioxane compound of the formula I according to claim 1, wherein $Z^1$ and $Z^2$ are single bonds, and $Z^3$ and $Z^4$ are either single bonds or —CH$_2$CH$_2$— groups.

5. A 1,3-dioxane compound of claim 1 of the formula

6. A 1,3-dioxane compound of claim 1 of the formula

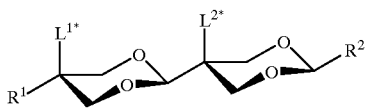

in which
 one of the radicals $L^{1*}$ and $L^{2*}$ is F and the other is H or F.

7. A 1,3-dioxane compound of claim 1 of the formula

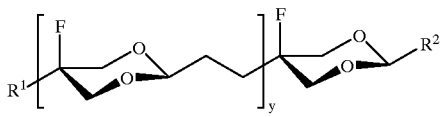

in which
 y is 1 or 2.

8. A liquid-crystalline medium which comprises at least one 1,3-dioxane compound according to claim 1.

9. A liquid-crystalline medium having at least two liquid-crystalline components, wherein at least one component is a 1,3-dioxane compound of the formula I according to claim 1.

10. A liquid-crystal display element, which comprises a liquid-crystalline medium according to claim 9.

11. An electro-optical display element, which comprises as dielectric, a liquid-crystalline medium according to claim 9.

12. A TFT or STN liquid-crystal display containing a liquid-crystal display element according to claim 10.

* * * * *